(12) United States Patent
Wolfe (10) Patent No.: US 9,069,927 B2
(45) Date of Patent: *Jun. 30, 2015

(54) ANTI-TERRORISM WATER QUALITY MONITORING SYSTEM

(75) Inventor: Thomas D. Wolfe, Grass Valley, CA (US)

(73) Assignee: Hach Company, Loveland, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,000

(22) Filed: Sep. 14, 2012

(65) Prior Publication Data

US 2013/0073611 A1 Mar. 21, 2013

Related U.S. Application Data

(60) Division of application No. 12/710,451, filed on Feb. 23, 2010, now Pat. No. 8,504,305, which is a division of application No. 12/272,018, filed on Nov. 17, 2008, now Pat. No. 7,698,073, which is a continuation of application No. 10/392,112, filed on Mar. 19, 2003, now Pat. No. 7,454,295, which is a continuation-in-part of application No. 10/055,225, filed on Oct. 26, 2001, now Pat. No. 6,560,543, which is a continuation-in-part of application No. 09/213,781, filed on Dec. 17, 1998, now Pat. No. 6,332,110.

(51) Int. Cl.
*G06F 19/00* (2011.01)
*B01D 61/12* (2006.01)
(Continued)

(52) U.S. Cl.
CPC ............ *G06F 19/709* (2013.01); *B01D 61/12* (2013.01); *B01D 61/22* (2013.01); *B01J 47/14* (2013.01); *C02F 1/008* (2013.01); *C02F 2209/001* (2013.01); *C02F 2209/003* (2013.01); *C02F 2209/006* (2013.01); *C02F 2209/008* (2013.01); *C02F 2209/02* (2013.01); *C02F 2209/05* (2013.01); *C02F 2209/06* (2013.01); *C02F 2209/11* (2013.01); *C02F 2209/29* (2013.01); *G01N 33/18* (2013.01); *G05B 21/02* (2013.01);
(Continued)

(58) Field of Classification Search
USPC ................ 702/22, 30–31, 188; 700/270, 271; 210/141, 634, 638, 660
See application file for complete search history.

(56) References Cited

U.S. PATENT DOCUMENTS

| 4,626,992 A | 12/1986 | Greaves et al. |
| 4,830,757 A | 5/1989 | Lynch et al. |

(Continued)

FOREIGN PATENT DOCUMENTS

| CA | 2283502 A1 | 9/1998 |
| EP | 0854839 A1 | 7/1998 |

(Continued)

OTHER PUBLICATIONS

International Search Report and Written Opinion dated Jul. 10, 2012, in Application No. PCT/IB2011/055238.

(Continued)

*Primary Examiner* — John Breene
*Assistant Examiner* — Hien Vo
(74) *Attorney, Agent, or Firm* — Miles & Stockbridge PC; James T. Carmichael (57) ABSTRACT

A method of monitoring advanced separation and/or ion exchange processes through the collection of localized data. The data is manipulated to generate preconfigured performance, maintenance, quality assurance, quality control, regulatory, cost reports, performance graphing and historical trends. The data is collected from sensors located at an equipment site and transferred to a remote located by use of the Internet, further all data received and used for generation of reports is also accessible by Internet connection.

19 Claims, 4 Drawing Sheets

(51) Int. Cl.
  *B01D 61/22* (2006.01)
  *B01J 47/14* (2006.01)
  *C02F 1/00* (2006.01)
  *G01N 33/18* (2006.01)
  *G05B 21/02* (2006.01)
  *G05B 23/02* (2006.01)
  *G06Q 20/20* (2012.01)
  *H04L 29/06* (2006.01)
  *G06Q 50/26* (2012.01)

(52) U.S. Cl.
  CPC ........ *G05B 23/0221* (2013.01); *G05B 23/0224* (2013.01); *G06Q 20/203* (2013.01); *H04L 67/42* (2013.01); *G06Q 50/265* (2013.01)

(56) References Cited

U.S. PATENT DOCUMENTS

| | | | |
|---|---|---|---|
| 5,227,038 A | 7/1993 | Smalley et al. | |
| 5,242,602 A | 9/1993 | Richardson | |
| 5,300,203 A | 4/1994 | Smalley | |
| 5,315,880 A | 5/1994 | Bailey | |
| 5,386,373 A | 1/1995 | Keeler et al. | |
| 5,451,314 A | 9/1995 | Neuenschwander | |
| 5,465,321 A | 11/1995 | Smyth | |
| 5,483,164 A | 1/1996 | Moss et al. | |
| 5,492,632 A | 2/1996 | Reber | |
| 5,494,573 A | 2/1996 | Schoenmeyer et al. | |
| 5,506,791 A | 4/1996 | Hungerford et al. | |
| 5,544,531 A | 8/1996 | Heckman | |
| 5,553,492 A | 9/1996 | Barrett et al. | |
| 5,556,517 A | 9/1996 | Smalley | |
| 5,591,312 A | 1/1997 | Smalley | |
| 5,608,171 A | 3/1997 | Hunter et al. | |
| 5,619,631 A | 4/1997 | Schott | |
| 5,631,744 A | 5/1997 | Takeuchi et al. | |
| 5,633,809 A | 5/1997 | Wissenbach et al. | |
| 5,644,088 A | 7/1997 | Heckman | |
| 5,646,863 A | 7/1997 | Morton | |
| 5,681,482 A | 10/1997 | Reber | |
| 5,691,914 A | 11/1997 | Randolph | |
| 5,739,376 A | 4/1998 | Bingel | |
| 5,754,451 A | 5/1998 | Williams | |
| 5,757,659 A | 5/1998 | Arai et al. | |
| 5,811,688 A | 9/1998 | Marsh et al. | |
| 5,826,029 A | 10/1998 | Gore et al. | |
| 5,832,410 A | 11/1998 | Lin et al. | |
| 5,835,724 A | 11/1998 | Smith | |
| 5,865,718 A | 2/1999 | Chan | |
| 5,867,483 A | 2/1999 | Ennis et al. | |
| 5,905,570 A | 5/1999 | White et al. | |
| 5,960,404 A | 9/1999 | Chaar et al. | |
| 5,970,426 A | 10/1999 | Mandel et al. | |
| 5,993,662 A | 11/1999 | Garr et al. | |
| 5,997,750 A | 12/1999 | Rozelle et al. | |
| 6,023,223 A | 2/2000 | Baxter, Jr. | |
| 6,061,603 A | 5/2000 | Papadopoulos et al. | |
| 6,064,148 A | 5/2000 | Tait et al. | |
| 6,097,995 A * | 8/2000 | Tipton et al. | 700/266 |
| 6,115,693 A | 9/2000 | McDonough et al. | |
| 6,129,901 A | 10/2000 | Moskovits et al. | |
| 6,149,775 A | 11/2000 | Tsuboi et al. | |
| 6,162,926 A | 12/2000 | Murphy et al. | |
| 6,167,376 A | 12/2000 | Ditzik | |
| 6,183,714 B1 | 2/2001 | Smalley et al. | |
| 6,208,943 B1 | 3/2001 | Randolph et al. | |
| 6,222,839 B1 | 4/2001 | Nakazaki et al. | |
| 6,265,466 B1 | 7/2001 | Glatkowski et al. | |
| 6,305,944 B1 | 10/2001 | Henry et al. | |
| 6,317,639 B1 | 11/2001 | Hansen | |
| 6,332,110 B1 | 12/2001 | Wolfe | |
| 6,346,023 B1 | 2/2002 | Tsuboi et al. | |
| 6,356,205 B1 | 3/2002 | Salvo et al. | |
| 6,359,444 B1 | 3/2002 | Grimes | |
| 6,370,448 B1 | 4/2002 | Eryurek | |
| 6,389,331 B1 | 5/2002 | Jensen et al. | |
| 6,399,785 B1 | 6/2002 | Murphy et al. | |
| 6,401,526 B1 | 6/2002 | Dal et al. | |
| 6,448,412 B1 | 9/2002 | Murphy et al. | |
| 6,463,352 B1 | 10/2002 | Tadokoro et al. | |
| 6,493,208 B1 | 12/2002 | Piche et al. | |
| 6,509,619 B1 | 1/2003 | Kendall et al. | |
| 6,530,160 B1 | 3/2003 | Gookins | |
| 6,538,153 B1 | 3/2003 | Hirsch et al. | |
| 6,560,543 B2 | 5/2003 | Wolfe et al. | |
| 6,577,988 B1 | 6/2003 | Travagline et al. | |
| 6,606,566 B1 | 8/2003 | Sunshine | |
| 6,618,709 B1 | 9/2003 | Sneeringer | |
| 6,645,455 B2 | 11/2003 | Margrave et al. | |
| 6,659,861 B1 | 12/2003 | Faris et al. | |
| 6,672,077 B1 | 1/2004 | Bradley et al. | |
| 6,673,314 B1 | 1/2004 | Burbank et al. | |
| 6,675,127 B2 | 1/2004 | LaBlanc et al. | |
| 6,683,783 B1 | 1/2004 | Smalley et al. | |
| 6,692,717 B1 | 2/2004 | Smalley et al. | |
| 6,712,864 B2 | 3/2004 | Horiuchi et al. | |
| 6,725,250 B1 | 4/2004 | Ellis, III | |
| 6,743,408 B2 | 6/2004 | Lieber et al. | |
| 6,748,748 B2 | 6/2004 | Bradley et al. | |
| 6,749,827 B2 | 6/2004 | Smalley et al. | |
| 6,752,977 B2 | 6/2004 | Smalley et al. | |
| 6,756,025 B2 | 6/2004 | Colbert et al. | |
| 6,756,026 B2 | 6/2004 | Colbert et al. | |
| 6,762,237 B2 | 7/2004 | Glatkowski et al. | |
| 6,790,425 B1 | 9/2004 | Smalley et al. | |
| 6,811,457 B2 | 11/2004 | Cheng et al. | |
| 6,824,755 B2 | 11/2004 | Colbert et al. | |
| 6,827,918 B2 | 12/2004 | Margrave et al. | |
| 6,830,679 B2 | 12/2004 | Tsuihiji et al. | |
| 6,836,737 B2 | 12/2004 | Petite et al. | |
| 6,845,336 B2 | 1/2005 | Kodukula et al. | |
| 6,847,739 B2 | 1/2005 | Jostschulte | |
| 6,852,410 B2 | 2/2005 | Veedu et al. | |
| 6,858,197 B1 | 2/2005 | Delzeit | |
| 6,863,942 B2 | 3/2005 | Ren et al. | |
| 6,872,330 B2 | 3/2005 | Mack et al. | |
| 6,875,412 B2 | 4/2005 | Margrave et al. | |
| 6,885,309 B1 | 4/2005 | Van Heteren | |
| 6,890,506 B1 | 5/2005 | Harutyunyan et al. | |
| 6,899,945 B2 | 5/2005 | Smalley et al. | |
| 6,900,264 B2 | 5/2005 | Kumar et al. | |
| 6,904,054 B1 | 6/2005 | Baum et al. | |
| 6,913,789 B2 | 7/2005 | Smalley et al. | |
| 6,921,575 B2 | 7/2005 | Horiuchi et al. | |
| 6,936,233 B2 | 8/2005 | Smalley et al. | |
| 6,936,653 B2 | 8/2005 | McElrath et al. | |
| 6,939,525 B2 | 9/2005 | Colbert et al. | |
| 6,947,427 B1 | 9/2005 | Rokugo et al. | |
| 6,949,237 B2 | 9/2005 | Smalley et al. | |
| 6,954,701 B2 | 10/2005 | Wolfe | |
| 6,961,641 B1 | 11/2005 | Forth et al. | |
| 6,969,504 B2 | 11/2005 | Smalley et al. | |
| 6,978,212 B1 | 12/2005 | Sunshine | |
| 6,979,709 B2 | 12/2005 | Smalley et al. | |
| 6,986,853 B2 | 1/2006 | Glatkowski et al. | |
| 6,988,925 B2 | 1/2006 | Arthur et al. | |
| 7,008,563 B2 | 3/2006 | Smalley et al. | |
| 7,008,604 B2 | 3/2006 | Smalley et al. | |
| 7,014,737 B2 | 3/2006 | Harutyunyan et al. | |
| 7,029,646 B2 | 4/2006 | Margrave et al. | |
| 7,036,324 B2 | 5/2006 | Bradley et al. | |
| 7,041,620 B2 | 5/2006 | Smalley et al. | |
| 7,048,999 B2 | 5/2006 | Smalley et al. | |
| 7,049,353 B2 | 5/2006 | Conroy et al. | |
| 7,052,666 B2 | 5/2006 | Colbert et al. | |
| 7,052,668 B2 | 5/2006 | Smalley et al. | |
| 7,058,154 B1 | 6/2006 | Stark et al. | |
| 7,060,241 B2 | 6/2006 | Glatkowski | |
| 7,061,749 B2 | 6/2006 | Liu et al. | |
| 7,067,098 B2 | 6/2006 | Colbert et al. | |
| 7,070,651 B1 | 7/2006 | Tolt et al. | |
| 7,070,754 B2 | 7/2006 | Smalley et al. | |
| 7,070,810 B2 | 7/2006 | Hirsch et al. | |
| 7,074,310 B2 | 7/2006 | Smalley et al. | |

(56) References Cited

U.S. PATENT DOCUMENTS

| | | |
|---|---|---|
| 7,076,871 B2 | 7/2006 | Horiuchi et al. |
| 7,085,938 B1 | 8/2006 | Pozzuoli et al. |
| 7,087,207 B2 | 8/2006 | Smalley et al. |
| 7,090,819 B2 | 8/2006 | Smalley et al. |
| 7,094,679 B1 | 8/2006 | Li et al. |
| 7,108,841 B2 | 9/2006 | Smalley et al. |
| 7,118,693 B2 | 10/2006 | Glatkowski et al. |
| 7,121,158 B2 | 10/2006 | Scott et al. |
| 7,176,877 B2 | 2/2007 | Tikhonski et al. |
| 7,179,561 B2 | 2/2007 | Niu et al. |
| 7,182,914 B2 | 2/2007 | Lai et al. |
| 7,189,314 B1 | 3/2007 | Pace et al. |
| 7,189,430 B2 | 3/2007 | Ajayan et al. |
| 7,195,754 B1 | 3/2007 | Glatkowski et al. |
| 7,204,970 B2 | 4/2007 | Smalley et al. |
| 7,217,650 B1 | 5/2007 | Ng et al. |
| 7,227,140 B2 | 6/2007 | Skidmore et al. |
| 7,250,148 B2 | 7/2007 | Yang et al. |
| 7,276,266 B1 | 10/2007 | Khare et al. |
| 7,282,191 B1 | 10/2007 | Choi et al. |
| 7,285,198 B2 | 10/2007 | Douglas |
| 7,303,875 B1 | 12/2007 | Bock et al. |
| 7,338,648 B2 | 3/2008 | Harutyunyan et al. |
| 7,338,915 B1 | 3/2008 | Smalley et al. |
| 7,342,479 B2 | 3/2008 | Glatkowski et al. |
| 7,342,506 B2 | 3/2008 | Paoli et al. |
| 7,345,307 B2 | 3/2008 | Pan et al. |
| 7,354,563 B2 | 4/2008 | Smalley et al. |
| 7,357,906 B2 | 4/2008 | Colbert et al. |
| 7,357,983 B2 | 4/2008 | Pfefferle et al. |
| 7,365,395 B2 | 4/2008 | Stumbo et al. |
| 7,378,040 B2 | 5/2008 | Luo et al. |
| 7,390,477 B2 | 6/2008 | Smalley et al. |
| 7,390,767 B2 | 6/2008 | Smalley et al. |
| 7,426,848 B1 | 9/2008 | Li et al. |
| 7,428,046 B2 | 9/2008 | Wang et al. |
| 7,452,735 B2 | 11/2008 | Li et al. |
| 7,454,295 B2 | 11/2008 | Wolfe |
| 7,465,494 B2 | 12/2008 | Ren et al. |
| 7,466,533 B2 | 12/2008 | Chow et al. |
| 7,468,315 B2 | 12/2008 | Buretea et al. |
| 7,470,620 B2 | 12/2008 | Dubin et al. |
| 7,473,411 B2 | 1/2009 | Ajayan et al. |
| 7,473,436 B1 | 1/2009 | Khare et al. |
| 7,479,240 B2 | 1/2009 | Jhi et al. |
| 7,514,369 B2 | 4/2009 | Li et al. |
| 7,515,333 B1 | 4/2009 | Empedocies |
| 7,522,040 B2 | 4/2009 | Passmore et al. |
| 7,553,371 B2 | 6/2009 | Dubrow et al. |
| 7,553,471 B2 | 6/2009 | Ohashi et al. |
| 7,557,028 B1 | 7/2009 | Scher et al. |
| 7,560,134 B2 | 7/2009 | Yaniv et al. |
| 7,560,136 B2 | 7/2009 | Ward et al. |
| 7,560,366 B1 | 7/2009 | Romano et al. |
| 7,563,722 B2 | 7/2009 | Yaniv et al. |
| 7,566,945 B2 | 7/2009 | Choi et al. |
| 7,569,503 B2 | 8/2009 | Pan et al. |
| 7,575,720 B2 | 8/2009 | Novak et al. |
| 7,575,933 B2 | 8/2009 | Gabriel et al. |
| 7,581,645 B2 | 9/2009 | Ho et al. |
| 7,595,528 B2 | 9/2009 | Duan et al. |
| 7,596,415 B2 | 9/2009 | Brabec et al. |
| 7,597,788 B2 | 10/2009 | Visel et al. |
| 7,611,740 B2 | 11/2009 | Jiang et al. |
| 7,611,906 B2 | 11/2009 | Yaniv |
| 7,623,972 B1 | 11/2009 | Li et al. |
| 7,628,974 B2 | 12/2009 | Grill et al. |
| 7,630,227 B2 | 12/2009 | Tran |
| 7,632,548 B2 | 12/2009 | Yaniv |
| 7,635,503 B2 | 12/2009 | Dominguez et al. |
| 7,641,938 B2 | 1/2010 | Liu et al. |
| 7,645,397 B2 | 1/2010 | Parce et al. |
| 7,647,813 B2 | 1/2010 | Pavlovsky |
| 7,651,769 B2 | 1/2010 | Dubrow |
| 7,651,944 B2 | 1/2010 | Duan et al. |
| 7,652,418 B2 | 1/2010 | Choi et al. |
| 7,655,497 B1 | 2/2010 | Yu et al. |
| 7,667,296 B2 | 2/2010 | Stumbo et al. |
| 7,687,981 B2 | 3/2010 | Parsapour |
| 7,691,720 B2 | 4/2010 | Furukawa et al. |
| 7,695,609 B2 | 4/2010 | Soundarrajan et al. |
| 7,696,272 B2 | 4/2010 | Li et al. |
| 7,698,073 B2 | 4/2010 | Wolfe |
| 7,701,014 B2 | 4/2010 | Mostarshed et al. |
| 7,701,428 B2 | 4/2010 | Stumbo et al. |
| 7,704,479 B2 | 4/2010 | Rinzler et al. |
| 7,704,547 B1 | 4/2010 | Delzeit et al. |
| 7,714,386 B2 | 5/2010 | Pesetski et al. |
| 7,714,398 B2 | 5/2010 | Ben-Barak et al. |
| 7,728,520 B2 | 6/2010 | Yaniv et al. |
| 7,736,209 B2 | 6/2010 | Mao et al. |
| 7,736,979 B2 | 6/2010 | Farrow et al. |
| 7,741,197 B1 | 6/2010 | Duan et al. |
| 7,745,498 B2 | 6/2010 | Pereira et al. |
| 7,749,477 B2 | 7/2010 | Jiang et al. |
| 7,750,235 B2 | 7/2010 | Scher et al. |
| 7,754,524 B2 | 7/2010 | Dubrow et al. |
| 7,755,038 B2 | 7/2010 | Niu et al. |
| 7,755,115 B2 | 7/2010 | Awano |
| 7,762,121 B2 | 7/2010 | Ng et al. |
| 7,767,067 B2 | 8/2010 | Silveri |
| 7,767,102 B2 | 8/2010 | Lemmi et al. |
| 7,767,270 B1 | 8/2010 | Khare et al. |
| 7,776,758 B2 | 8/2010 | Duan et al. |
| 7,776,760 B2 | 8/2010 | Taylor |
| 7,782,462 B2 | 8/2010 | Pavlovsky |
| 7,784,531 B1 | 8/2010 | Li et al. |
| 7,785,922 B2 | 8/2010 | Robbins |
| 7,786,024 B2 | 8/2010 | Stumbo et al. |
| 7,786,402 B2 | 8/2010 | Fink et al. |
| 7,791,258 B2 | 9/2010 | Yaniv et al. |
| 7,794,600 B1 | 9/2010 | Buretea et al. |
| 7,795,125 B2 | 9/2010 | Buretea et al. |
| 7,801,687 B1 | 9/2010 | Li et al. |
| 8,504,305 B2 | 8/2013 | Wolfe |
| 8,577,623 B2 | 11/2013 | Wolfe |
| 2001/0020195 A1 | 9/2001 | Patel et al. |
| 2001/0053992 A1 | 12/2001 | Eto et al. |
| 2001/0055978 A1 | 12/2001 | Herrod et al. |
| 2002/0023479 A1 | 2/2002 | Burge et al. |
| 2002/0130069 A1 | 9/2002 | Moskoff |
| 2002/0133270 A1 | 9/2002 | Hung et al. |
| 2002/0183971 A1 | 12/2002 | Wegerich et al. |
| 2003/0052585 A1 | 3/2003 | Guillorn et al. |
| 2003/0089899 A1 | 5/2003 | Lieber et al. |
| 2003/0124717 A1 | 7/2003 | Awano et al. |
| 2003/0174070 A1 | 9/2003 | Garrod et al. |
| 2003/0207326 A1 | 11/2003 | Su et al. |
| 2004/0026684 A1 | 2/2004 | Empedocles |
| 2004/0066313 A1 | 4/2004 | Ong et al. |
| 2004/0117731 A1 | 6/2004 | Blyashov |
| 2004/0132070 A1 | 7/2004 | Star et al. |
| 2004/0136866 A1 | 7/2004 | Pontis et al. |
| 2004/0245209 A1 | 12/2004 | Jung et al. |
| 2005/0046017 A1 | 3/2005 | Dangelo |
| 2005/0136483 A1 | 6/2005 | Carlson |
| 2005/0186333 A1 | 8/2005 | Douglas |
| 2005/0221473 A1 | 10/2005 | Dubin et al. |
| 2005/0224220 A1 | 10/2005 | Li et al. |
| 2005/0269285 A1 | 12/2005 | Jung et al. |
| 2005/0273424 A1 | 12/2005 | Silverman et al. |
| 2006/0014155 A1 | 1/2006 | Hamers et al. |
| 2006/0078468 A1 | 4/2006 | Gabriel et al. |
| 2006/0112983 A1 | 6/2006 | Parce et al. |
| 2006/0124028 A1 | 6/2006 | Huang et al. |
| 2006/0240218 A1 | 10/2006 | Parce |
| 2006/0257637 A1 | 11/2006 | Pereira et al. |
| 2006/0275914 A1 | 12/2006 | Henley et al. |
| 2006/0287906 A1 | 12/2006 | McGillin |
| 2007/0044295 A1 | 3/2007 | Chen |
| 2007/0045128 A1 | 3/2007 | Krafthefer et al. |
| 2007/0132043 A1 | 6/2007 | Bradley et al. |
| 2007/0140930 A1 | 6/2007 | Novak et al. |
| 2007/0155064 A1 | 7/2007 | Chen et al. |

(56) References Cited

U.S. PATENT DOCUMENTS

| | | |
|---|---|---|
| 2007/0163965 A1 | 7/2007 | Wolfe |
| 2007/0238209 A1 | 10/2007 | Yaniv et al. |
| 2007/0246364 A1 | 10/2007 | Amlani et al. |
| 2008/0035481 A1 | 2/2008 | McCormack et al. |
| 2008/0142361 A1 | 6/2008 | Han et al. |
| 2008/0150009 A1 | 6/2008 | Chen |
| 2008/0152839 A1 | 6/2008 | Han et al. |
| 2008/0221806 A1 | 9/2008 | Bryant et al. |
| 2008/0237540 A1 | 10/2008 | Dubrow |
| 2008/0246076 A1 | 10/2008 | Chen |
| 2008/0280069 A1 | 11/2008 | Parce et al. |
| 2008/0280780 A1 | 11/2008 | Hamers et al. |
| 2009/0035570 A1 | 2/2009 | Mao et al. |
| 2009/0045061 A1 | 2/2009 | Farrow et al. |
| 2009/0058431 A1 | 3/2009 | Dass et al. |
| 2009/0072192 A1 | 3/2009 | Seal et al. |
| 2009/0095704 A1 | 4/2009 | Mao et al. |
| 2009/0123343 A1 | 5/2009 | Kwiatkowski |
| 2009/0124025 A1 | 5/2009 | Hamilton et al. |
| 2009/0138240 A1 | 5/2009 | Wolfe |
| 2009/0192429 A1 | 7/2009 | Daniels et al. |
| 2009/0198117 A1 | 8/2009 | Cooper et al. |
| 2009/0230380 A1 | 9/2009 | Leon et al. |
| 2009/0242429 A1 | 10/2009 | Sitdikov et al. |
| 2009/0242854 A1 | 10/2009 | Li et al. |
| 2009/0252886 A1 | 10/2009 | Barker et al. |
| 2009/0261186 A1 | 10/2009 | Fink et al. |
| 2009/0274833 A1 | 11/2009 | Li et al. |
| 2009/0278556 A1 | 11/2009 | Man et al. |
| 2009/0286383 A1 | 11/2009 | Jiang et al. |
| 2009/0325370 A1 | 12/2009 | Yang et al. |
| 2010/0000762 A1 | 1/2010 | Yang et al. |
| 2010/0055349 A1 | 3/2010 | Gaitas et al. |
| 2010/0062178 A1 | 3/2010 | Zhang et al. |
| 2010/0068406 A1 | 3/2010 | Man |
| 2010/0072429 A1 | 3/2010 | Rajala et al. |
| 2010/0089122 A1 | 4/2010 | Abdullah et al. |
| 2010/0102245 A1 | 4/2010 | Jiang et al. |
| 2010/0104808 A1 | 4/2010 | Fan et al. |
| 2010/0116666 A1 | 5/2010 | Park et al. |
| 2010/0127167 A1 | 5/2010 | Schropp, Jr. et al. |
| 2010/0140213 A1 | 6/2010 | Mizukami et al. |
| 2010/0143234 A1 | 6/2010 | Kajiuyra et al. |
| 2010/0153021 A1 | 6/2010 | Wolfe |
| 2010/0167011 A1 | 7/2010 | Dubrow |
| 2010/0167512 A1 | 7/2010 | Pan et al. |
| 2010/0173228 A1 | 7/2010 | Wallace et al. |
| 2010/0204924 A1 | 8/2010 | Wolfe et al. |
| 2010/0332149 A1 | 12/2010 | Scholpp |
| 2011/0125412 A1 | 5/2011 | Salzer et al. |
| 2012/0125771 A1 | 5/2012 | Salzer et al. |
| 2013/0009781 A1 | 1/2013 | Wolfe |
| 2013/0013259 A1 | 1/2013 | Wolfe |
| 2013/0073611 A1 | 3/2013 | Wolfe |

FOREIGN PATENT DOCUMENTS

| | | |
|---|---|---|
| EP | 1015384 A1 | 7/2000 |
| EP | 1404908 B1 | 11/2007 |
| EP | 1864122 A2 | 12/2007 |
| EP | 1623437131 | 12/2007 |
| EP | 1954387 A2 | 8/2008 |
| EP | 1976431 A2 | 10/2008 |
| EP | 1836104 B1 | 1/2009 |
| EP | 2018549 A2 | 1/2009 |
| EP | 2047531 A | 4/2009 |
| EP | 2012589 B1 | 7/2009 |
| EP | 2083928 A1 | 8/2009 |
| EP | 1556878 B1 | 4/2010 |
| JP | 3958792 B2 | 8/2007 |
| JP | 3962376 B2 | 8/2007 |
| JP | 2008/260073 | 10/2008 |
| JP | 4381428 B2 | 12/2009 |
| WO | WO 97/09272 A1 | 3/1997 |
| WO | WO 00/36412 A1 | 6/2000 |
| WO | WO 01/80494 | 10/2001 |
| WO | WO 03/024798 A1 | 3/2003 |
| WO | WO03/038685 A2 | 5/2003 |
| WO | WO 03/050036 A1 | 6/2003 |
| WO | WO 03/078317 A1 | 9/2003 |
| WO | WO 2004/024407 A1 | 3/2004 |
| WO | WO 2004/052559 A2 | 6/2004 |
| WO | WO 2004/063964 (A2) | 7/2004 |
| WO | WO 2004/069737 A2 | 8/2004 |
| WO | WO 2004/097853 A1 | 11/2004 |
| WO | WO 2005/022120 A2 | 3/2005 |
| WO | WO 2005/079202 A2 | 9/2005 |
| WO | WO 2005/086982 A2 | 9/2005 |
| WO | WO 2005/110624 A2 | 11/2005 |
| WO | WO 2006/069458 A1 | 7/2006 |
| WO | WO 2006/073420 A2 | 7/2006 |
| WO | WO 2006/078286 A2 | 7/2006 |
| WO | WO 2006/102064 A2 | 9/2006 |
| WO | WO 2007/024697 A2 | 3/2007 |
| WO | WO 2007/067922 A2 | 6/2007 |
| WO | WO 2007/106836 A2 | 9/2007 |
| WO | WO 2007/124612 A2 | 11/2007 |
| WO | WO 2008/051205 A2 | 5/2008 |
| WO | WO 2008/057615 A2 | 5/2008 |
| WO | WO 2008/076473 A2 | 6/2008 |
| WO | WO 2008/091402 A2 | 7/2008 |
| WO | WO 2008/060455 A3 | 11/2008 |
| WO | WO 2008/143714 A2 | 11/2008 |
| WO | WO 2008/150336 A2 | 12/2008 |
| WO | WO 2009/011450 A1 | 1/2009 |
| WO | WO 2009/023061 A2 | 2/2009 |
| WO | WO 2009/042079 A2 | 4/2009 |
| WO | WO 2008/106426 A9 | 10/2009 |
| WO | WO 2010/003212 A1 | 1/2010 |
| WO | WO 2010/048405 A1 | 4/2010 |
| WO | WO 2010/048407 A1 | 4/2010 |
| WO | WO 2010/056826 A1 | 5/2010 |
| WO | WO 2010/077226 A1 | 7/2010 |
| WO | WO 2010/093703 A1 | 8/2010 |
| WO | WO 2010096035 A1 | 8/2010 |
| WO | WO 2012/069993 A2 | 5/2012 |
| WO | WO 2012/069992 A2 | 9/2012 |

OTHER PUBLICATIONS

International Search Report and Written Opinion dated Aug. 30, 2012, in Application No. PCT/IB2011/055240.
U.S. Appl. No. 11/331,721, filed Jan. 13, 2006.
U.S. Appl. No. 12/565,091, filed Sep. 23, 2009.
U.S. Appl. No. 12/710,451, filed Feb. 23, 2010.
U.S. Appl. No. 12/874,293, filed Sep. 2, 2010.
U.S. Appl. No. 12/952,566, filed Nov. 23, 2010.
U.S. Appl. No. 12/952,392, filed Nov. 23, 2010.
U.S. Appl. No. 13/619,775, filed Sep. 14, 2012.
U.S. Appl. No. 13/619,880, filed Sep. 14, 2012.
Cycliax, Ingo, "Remote Internet Data Logging and Sensing", Circuit Cellar Magazine, Embedded PC, PC/104 Quarter104, Nov. 1997, pp. 53-59.
McKinnon, et al., "Automating Communications with and Developing User Interfaces for Remote data Acquisition and Analysis Systems", IEEE Transactions on Nuclear Science, vol. 44, No. 3, Jun. 1997, pp. 1062-1064.
Franklin, et al., "Data in Your Face": Push Technology in Perspective, S., SIGMOD Record, vol. 27, Issue 2, Jun. 1998, pp. 516-519.
Soreide, et al., "Mosaic Access to Realtime Data from the TOGA-TAO array of moored buoys", accessed from web site Equatorial Pacific, Oct. 16, 2002, pp. 1-8.
Northwest Fisheries Science Center, National Marine Fisheries Service (NOAA), "Water Recirculation Project", accessed from web site NWFSC:Aquaculture-Water Recirculation Project, Oct. 16, 2002, pp. 1-3.
Northwest Fisheries Science Center, "NWFSC Water Recirculation Project: Data Acquisition and Web Display", accessed from web site NWFSC Web Template, Oct. 16, 2002, pp. 1-3.

(56) References Cited

OTHER PUBLICATIONS

Scott, et al., "A Computer Automated Cold Water Recirculating System for Aquaculture Research", accessed from web U.S. Dept. Commerce/NOAA/NMFS/NWFSC, Oct. 16, 2002, pp. 1-9.

Remote Measurement Systems, "Case Studies", accessed from web site Remote Measurement Systems—Case Studies: Fisheries, Oct. 16, 2002, pp. 1-4.

Remote Measurement Systems, "Posting Real-Time Measurement to the Web", Home Energy, accessed from web site Posting Real-Time Measurements to Web Pages, Oct. 16, 2002, pp. 1-5.

Liu et al., Carbon Nanotube in Biology and Medicine: In vitro and in vivo Detection, Imaging and Drug Delivery; Nano Res., Vole 2, pp. 85-120 (2009).

Tzeng et al., "Hydration Properties of Carbon Nanotubes and Their Effects on Electrical and Biosensor Applications", New Diamond and Frontier Carbon Technology, vol. 14, No. 3, pp. 193-201.

Ardakan, Mohammad Mazloum et al.,: "Novel Coated-Wire Membrane Sensor Based on Bis(Acetylacetonato) Cadmium(II) for the Determination of Chromate Ions"; Department of Chemistry, Faculty of Science, Kashan University, Kashan, Iran; received Jul. 24, 2004; accepted Nov. 16, 2004; published online Mar. 21, 2005 © Springer-Verlag 2005.

Schuler, R. et al., Modified gas-permeable silicone rubber membranes for covalent immobilization of enzymes and their use in biosensor development ICB, Institut fur Chemo- and Biosensorik, eV, Mendelstrasse 7, D-48149 Munster, Germany, received Apr. 13, 1999, accepted Jun. 18, 1999.

Faridbod, Farmoush et al.; "The fabrication of potentiometric membrane sensors and their applications"; Tehran, P.O. Box 14155-6451, Iran, accepted Nov. 12, 2007; African Journal of Biotechnology vol. 6 (25), pp. 2960-2987, Dec. 28, 2007. Available online at http://www.academicjournals.org/AJ; ISSN 1684-5315 © 2007 Academic Journals.

Zbignlew, Moron, "Considerations on the Accuracy of Measurements of Electrical Conductivity of Liquids" Department of Biomedical Engineering and Instrumentation, Wroclaw University of Technology, Wroclase, Poland, XVIII Imeko World Congress Metrology for a Sustainable Development, Sep. 17-22, 2006, Rio de Janeiro, Brazil.

Heng, Lee Yook et al., "Producing "Self-Plasticizing" Ion-Selective Membranes", Institute of Biotechnology, University of Cambridge, Tennis Court Road, Cambridge CB2 1QT, U.K. Anal. Chem. 2000, 72, 42-51.

Pretsch, Emo et al., "Design features of ionophores for ion selective electrodes", Department of Organic Chemistry, Swiss Federal Institute of Technology (ETH), Universitatstrasse 16, CH-8092 Zurich, Switzerland, Pure & Appl. Chem., vol. 60, No. 4, pp. 567-574, 1988, printed in Great Britain © 1998 IUPAC.

Buhrer, Thomas, "Neutral-Carrier-Based Ion-Selective Microelectrodes Design and Application, A Review", Department of Organic Chemistry, Swiss Federal Institute of Technology, Zurich, Switzerland, Analytical Sciences, Dec. 1988, vol. 4, pp. 547-557.

Lumb Alan M. et al., "Users Manual for an Expert System (HSPEXP) for Calibration of the Hydrological Simulation Program—Fortran", U. S. Geological Survey, Water-Resources Investigation Report 94-4168, 1994, 106 pages.

Johnston et al., "Management, Operation and Maintenance of Irrigation and Drainage Systems", Second Edition, ASCE Manuals and Reports on Engineering Practive No. 57, American Society of Civil Engineers, 1991, 13 pages.

Final Rejection dated Jul. 19, 2013 in U.S. Appl. No. 13/619,880.

Notice of Allowance dated Aug. 7, 2013, in U.S. Appl. No. 13/619,775.

Nonfinal Office Action dated Sep. 12, 2013, in U.S. Appl. No. 12/565,091.

Final Rejection dated Sep. 13, 2013, in U.S. Appl. No. 12/952,566.

Nonfinal Office Action dated Sep. 13, 2013, in U.S. Appl. No. 11/331,721.

Final Rejection dated Sep. 26, 2013, in U.S. Appl. No. 12/952,392.

French Search Report dated May 29, 2013, in French Patent Application No. 11 6006.

Nonfinal Office Action dated Jan. 31, 2013, in U.S. Appl. No. 13/619,880.

Nonfinal Office Action dated Mar. 4, 2013, in U.S. Appl. No. 13/619,775.

International Preliminary Report on Patentability dated Jun. 6, 2013, in PCT/IB2011/055240.

International Preliminary Report on Patentability dated Jun. 6, 2013, in PCT/IB2011/055238.

Nonfinal Office Action dated Nov. 19, 2013, in U.S. Appl. No. 13/619,880.

Final Rejection dated May 7, 2014, in U.S. Appl. No. 11/331,721.

Final Rejection dated May 6, 2014, in U.S. Appl. No. 12/565,091.

Final Rejection dated May 15, 2014, in U.S. Appl. No. 13/619,880.

Nonfinal Office Action dated Jun. 3, 2014, in U.S. Appl. No. 14/062,976.

Notice of Allowance dated Sep. 11, 2014, in U.S. Appl. No. 14/062,976.

Notice of Allowance dated Oct. 3, 2014, in U.S. Appl. No. 12/565,091.

French Search Report dated May 29, 2013, in French Patent Application No. 11 60667, 6 pages.

European Office Action dated Sep. 30, 2014, in European Application No. 03 815 260.9-1559.

Canadian Office Action dated May 17, 2012, in Canadian Application No. 2,512,643.

Bohme, Thomas J. et al., "Comparison of Autoassociative Neural Networks and Kohonen Maps for Signal Failure Detection and Reconstruction", Jan. 1, 1999 XP055050318, Retrieved from the Internet: URL:http//citeseerx.ist.psu.edu/viewdoc/download?doi=10.1.1.39,4334&rep=rep1&type=pdf [retrieved on Jan. 18, 2013].

Lindquist M. et al., "Virtual water quality tests with an electronic tongue", IMTC 2001, Proceedings of the $18^{TH}$, IEEE Instrumentation and Measurement Technology Conference, Budapest, Hungary, May 21-23, 2001; [IEEE Instrumentation and Measurement Technology Conference. (IMTC):] New York, NY: IEEE, US, vol. 2, May 21, 2001, pp. 1320-1324, XP010545970, DOI: 10.1109/IMTC.2001.928288 ISBN: 978-0-7803-6646-6.

Bourgeois W., et al.: "Use of a chemical sensor array for detecting pollutants in domestic wastewater", Water Research, Elsevier, Amsterdam, NL, vol. 36, No. 18, Nov. 1, 2002, pp. 4505-4512, XP004380734, ISSN: 0043-1354, DOI: 10.1016/S0043(02)00183-5.

Nonfinal Office Action dated Dec. 11, 2014, in U.S. Appl. No. 13/619,880.

Notice of Allowance dated Jan. 14, 2015, in U.S. Appl. No. 11/331,721.

\* cited by examiner

ANTI-TERRORISM WATER QUALITY MONITORING SYSTEM

CROSS-REFERENCE TO RELATED APPLICATIONS

This application is a divisional of application Ser. No. 12/710,451 filed Feb. 23, 2010, which is a divisional of application Ser. No. 12/272,018 filed Nov. 17, 2008 (now U.S. Pat. No. 7,698,073 issued Apr. 13, 2010), which is a continuation of application Ser. No. 10/392,112 filed Mar. 19, 2003 (now U.S. Pat. No. 7,454,295 issued Nov. 18, 2008), which is a continuation-in-part of application Ser. No. 10/055,225 filed Oct. 26, 2001 (now U.S. Pat. No. 6,560,543 issued May 6, 2003), which is a continuation-in-part of application Ser. No. 09/213,781 filed Dec. 17, 1998 (now U.S. Pat. No. 6,332,110 issued Dec. 18, 2001).

FIELD OF THE INVENTION

This invention is related to the field of water treatment, and in particular, to a method of monitoring advanced separation and/or ion exchange processes by use of the world wide web allowing review of data collected and complied asynchronously from a web server.

BACKGROUND OF THE INVENTION

It is well recognized that nearly every aspect of manufacturing, as well as life itself, is dependant upon water. Water includes an infinite combination of cations and anions, metals, turbidity, dissolved solids, and so forth, all of which combine to form unique water chemistries. Technology provides the ability to adjust, reduce, or remove such constitutes which can effectively prepare water for use in a particular application. Proper water treatment provides an economically way of conditioning water to a predetermined quality level as required for the particular application.

For instance, municipal water may be obtained from any source, including seawater, all of which can be made potable by use of proper water treatment equipment. A reverse osmosis system, with minimal pretreatment, is capable of lowering the total dissolved solids of sea water into drinking water. Despite the sophistication of pretreatment, improper monitoring can allow seawater to quickly foul membranes. However, if the fouling is monitored properly, the membranes can be easily cleaned and the system will continue to run a design specifications. If the fouling is not detected quickly through proper monitoring, the membranes can be irreparably damaged requiring partial or total membrane replacement. The cost of unplanned membrane replacement, not including the revenues typically associated with down time, can make such a system cost prohibitive.

As yet another example, water is also required for steam generation in nuclear reactors. The boilers operate at a super heat which requires a very high quality of water, such as that produced by ion exchange. In this situation, it is critical that the process system is monitored properly to avoid expensive boiler cleanings and the associated down time. Such systems may also include the need to monitor hazardous boiler chemicals, such as hydrazine, requiring highly qualified personnel.

Yet another example of a manufacturer requiring very advanced separation and/or ion exchange processes are the manufacturers of microprocessors. This type of manufacturing requires an ultra-pure water quality. Again it is most critical that the water treatment process system is monitored properly to avoid latent defects in the microprocessors.

Thus, no matter what water is used for, if it requires advanced separation and/or ion exchange processes to obtain the quality required, proper monitoring of the equipment is absolutely critical. It is well recognized that the better the monitoring, the water treatment system will operate economically and reliably.

One of the problems with maintaining advanced processing equipment is a need for highly qualified individuals. Employment of a full time staff is costly and can be problematic since such monitoring is repetitively and highly qualified individuals can easily become bored. For this reason, all advanced separation processes include a large assortment of strategically placed sensors that are typically incorporated into a computer system capable of comparing the sensor values against a pre-set quality level. However, if the operator does not recognize a particular alarm condition, the elaborate array of monitoring equipment is useless.

In an effort to lessen this well recognized problems, systems have been developed for use in transferring information to a remote site for back-up monitoring of the employee's duties. However, a simple remote monitor maintains the requirement that the individual monitoring the equipment is capable of determining, what he believes, is a controllable situation. This exposes a company to the expertise of a particular employee and unless the equipment owner has a secondary source to verify operation of the equipment, loss product, loss profit, and down time will still occur.

Thus, what is lacking in the art, is a means for monitoring advanced separation and/or ion exchange processes in a cost effective manner by highly trained personnel providing the consumer with a real time analysis and economic progression of their particular equipment that can be viewed and verified at any time and from any location having access to the Internet.

SUMMARY OF THE INVENTION

The instant invention is a method of monitoring advanced separation and/or ion exchange processes through the collection of data which is manipulated to generate preconfigured performance, maintenance, quality assurance, quality control, regulatory, cost reports, performance graphing and historical trends. The data is collected from sensors located at an equipment site and transferred to a remote located by use of the Internet where all data received can be used for the generation of reports also accessible by Internet connection.

The reports, graphs and information are viewed online or downloaded by use of a web browser. The method allows a single location to monitor countless customers with each customer capable of reviewing information relevant to their equipment, all information is kept confidential by use of appropriate account names, protocols and passwords.

Thus, an objective of the instant invention is to provide a method of compiling information from a plurality of sensors mounted to advanced separation and/or ion exchange processing equipment to generate plant process, operating and economic information accessible in near real time, from any location having access to the Internet.

Another objective of the instant invention is to provide a system that operates independent of all system controls wherein no feedback is possible to the programmable logic controller or control system and to transfer such information by a local Internet provider to a consolidating Internet address.

Yet another objective of the instant invention is to provide an Internet monitoring system that can be viewed online or offline providing alarms by the use of current and historical records, providing scheduled and predicted maintenance requirements by the use of the current and historical records; providing emergency notification of failures, shutdowns, critical parameters, membrane damage by the use of electronic mail, pager, and/or human voice calling. The data is acquired from either a data capture module or by use of an improved PLC interface. Sensors are arranged to provide logical functional groupings for review and analysis (e.g. pretreatment, RO/MF train #1, /MF train #2, post treatment, ion exchange and so forth. Specific water treatment configurations include the normalization, calculations applicable to the monitoring and performance and analysis of membrane systems.

Another objective of the instant invention is to provide a method of monitoring advanced separation and/or ion exchange processes in a relatively moderate cost to the consumer while providing information that is accurate, dependable, and near real-time by use of relatively simply architecture.

Another objective of the instant invention is to provide a method of monitoring advanced separation and/or ion exchange processes which is independent and/or complimentary of the existing monitoring system.

The further objective of this invention is to provide a widely understood user interface between the underlying data generated by a process system such as the production of ultra pure water for semiconductor manufacturing and the corporate managers ultimately responsible for the entire facility's operation. Although many commercially available systems make data available from process systems over the Internet, heretofore these systems have been difficult to learn to manipulate in a facile manner. The present invention overcomes these limitations by presenting data in the context of the by now familiar web browser such as Netscape Navigator or Internet Explorer. This data is furthermore already analyzed and formatted in a configuration that allows even non-technical personnel to readily grasp the current state of system performance.

It is readily apparent that this same approach could easily be applied to other water using or water processing applications. For example, municipal water treatment and sewage treatment plants are ultimately the responsibility of elected officials. Yet these officials rarely have the technical training or time to allow them directly access the performance parameters of the systems for which they are responsible. The present invention could easily be used to provide a readily understandable presentation of the current performance of municipal water treatment system which was fully accessible by the elected officials at any time via the Internet. In addition, in this application of the technology, the same presentation of the system performance could be made accessible to the public at large, allowing interested members of the public to monitor the operation of their own drinking water plants as desired.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
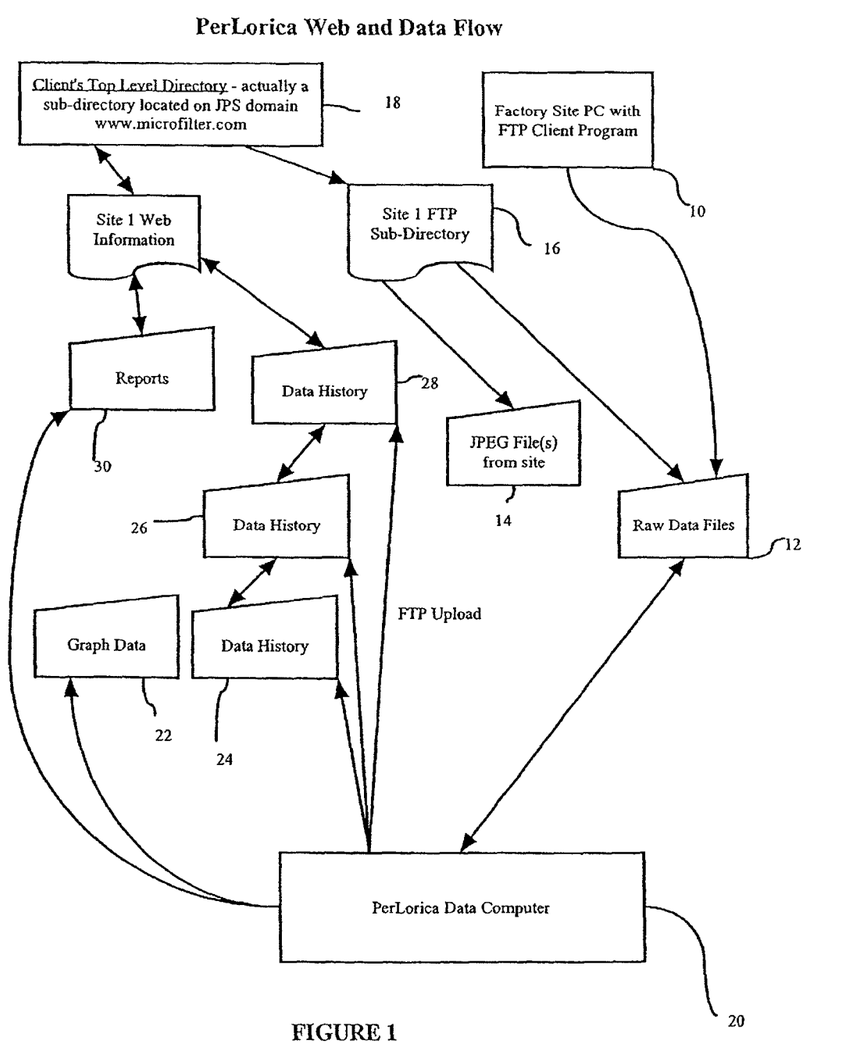
FIG. 1 is a pictorial representation of the various modules that make up the instant invention.

The instant invention is a monitoring system that incorporates the use of the Internet for providing a remote location for assimilation and dissemination of configured reports regarding advanced separation and/or ion exchange processes. Data is first collected by the use of sensors and on-line analytical devices from numerous locations on a water treatment system. For instance, a typical micro filter or reverse osmosis sensor group would include, but is not limited to: raw water temperature, conductivity, PH, pressure, and turbidity; permeate flow, turbidity, pressure, and conductivity; concentrate flow and pressure as well as on/off operation of the operating pump. The data generated by the sensors and on-line liquid devices are forwarded to a data capture module or programmable controller 10 which performs the required analog to digital conversion for use in transmitting data files 12 and 14 to a main server located off-site by use of local Internet access. Date files may also be transferred by modem to a processing site. The local data capture module, or programmable controller 10, continuously scans sensor data inputs and automatically logs and archives operating data at specified intervals. System operation for real time monitoring 16 by accessing an Internet web site 18 specifically set up for a particular customer. The data is also manipulated by the data computer 20 with ftp uploads wherein operating parameters are displayed graphically in a tabular format which are color coded to provide an indication of normal operation, warning status or alarm conditions. The information from the sensors are used for determining critical information for the proper evaluation of reverse osmosis membrane performance per (salt rejection, permeate flow; feed/brine average rejection and simple rejection) which is normalized in accordance with AST Standards and graphically displayed for performance evaluation, preventative maintenance, scheduling, or for trouble shooting.

Historical performance data 24 can be plotted and presented also in geographical 26 or tabular form 28 for selected periods. This provides for not only an historical analysis of system performance, but also a record of prior performance where quality control or regulatory recording purposes. In this manner, the software is designed to continuously scan sensor input and compare the current value with alarm set points in a pre-determined report 30. These set points may be different than actual locally set alarm points. For example, management may wish to see all instances where alarms were close to an alarm or trigger point and such conditions may be summarized in exception reports. The device further has the ability to notify authorized users by E-mail or use of a pager when process conditions meet or exceed, or appear likely to exceed, normal alarm conditions. This provides a layer of redundancy in system operation, and allows non technical and management personnel to be notified promptly in the event of non standard operations.

The customer is capable of accessing data related to his processing equipment including all data, information and reports by use of any computer having Internet access capability. This eliminates the need for specialized equipment and allows a manager operating at his desk to access the data from any location whether it be the office, home, or on the road without the use of specialized computer systems. The software program continually updates the reports for the customer or a customer may view the reports or download them from the web site.

In the preferred embodiment, the reports are configured to each customer's requirements when a service agreement is established, the reports are typically generated for three primary management levels: A) Process systems operations, B) Plant QA/QC and C) financial oversight. For instance, the process system operations would contain the information necessary to monitor, maintain, supervise and trouble shoot process plant system performance. In this manner the typical information and parameters process block would include, if applicable, flow rates, pressures, delta pressures, permeate and/or ion exchange quality, ph, alarm conditions, tank levels, and a graphical presentation of applicable process performance parameters and trends. A Plant QA/QC report would contain the information necessary to enable plant managers to effectively manage downstream manufacturing or distribution processes. In addition, quality assurance personnel would be able to monitor the quality and quantity of the treated water to confirm compliance with specifications and standards. Information in this report would typically include treated water production rate (flow), treated water consumption rate (flow), treated water storage volume, reserve capacity (at current production and consumption rates), final treated water quality, reports and archive data for regulatory compliance and/or QA/QC documentation.

Financial oversight would be through a plant economic report which would contain information needed by managers with profit and loss or budget responsibility to effectively track the cost of operation and to identify budget variances, when they occur, to permit timely corrective action. In this manner, typical information parameters contained in a plant economic report would include calculated power consumption (expressed in kWh and actual cost in local currency) and computed on the basis of user's supply pump/motor efficiencies both as a year to date, as a percent of the prior period, and variances both actual and budget/actual versus prior period. The parameter would also include calculated chemical consumption (expressed in volume consumption and as converted to local currency) and computed based on the user's supplied chemical dose rates and integrated feed water flow rates. This would be performed as a year to date, as a percent of the prior period, as variances both actual versus budget/actual versus prior period.

Calculated raw water consumption based on integrated water use from feed water flow rates calculated on the year to date, as a percent of the prior period, and as variances-actual versus budget/actual versus prior period.

Projected membrane element life to be provided estimated upon the operational life remaining (based on current performance and trends) and estimated sinking fund value for membrane replacement.

Calculated/estimated overall plant efficiency may be provided as a percent of theoretical efficiency. Efficiency could be based on the theoretical minimum water, power, and chemical consumption versus actual consumption calculated.

Figure 2:
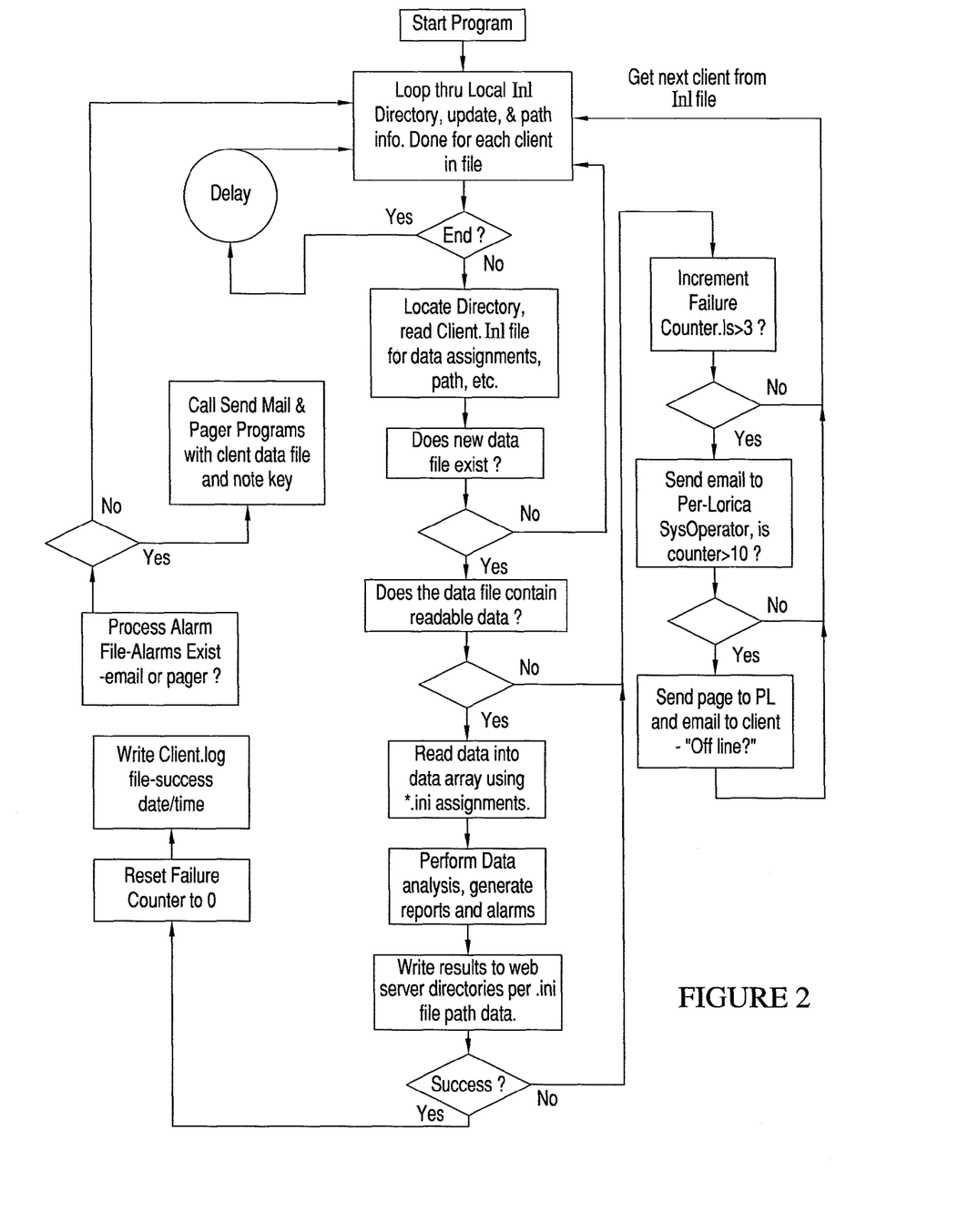
FIG. 2 is a flow diagram of the start-up operations of the software.
Figure 3:
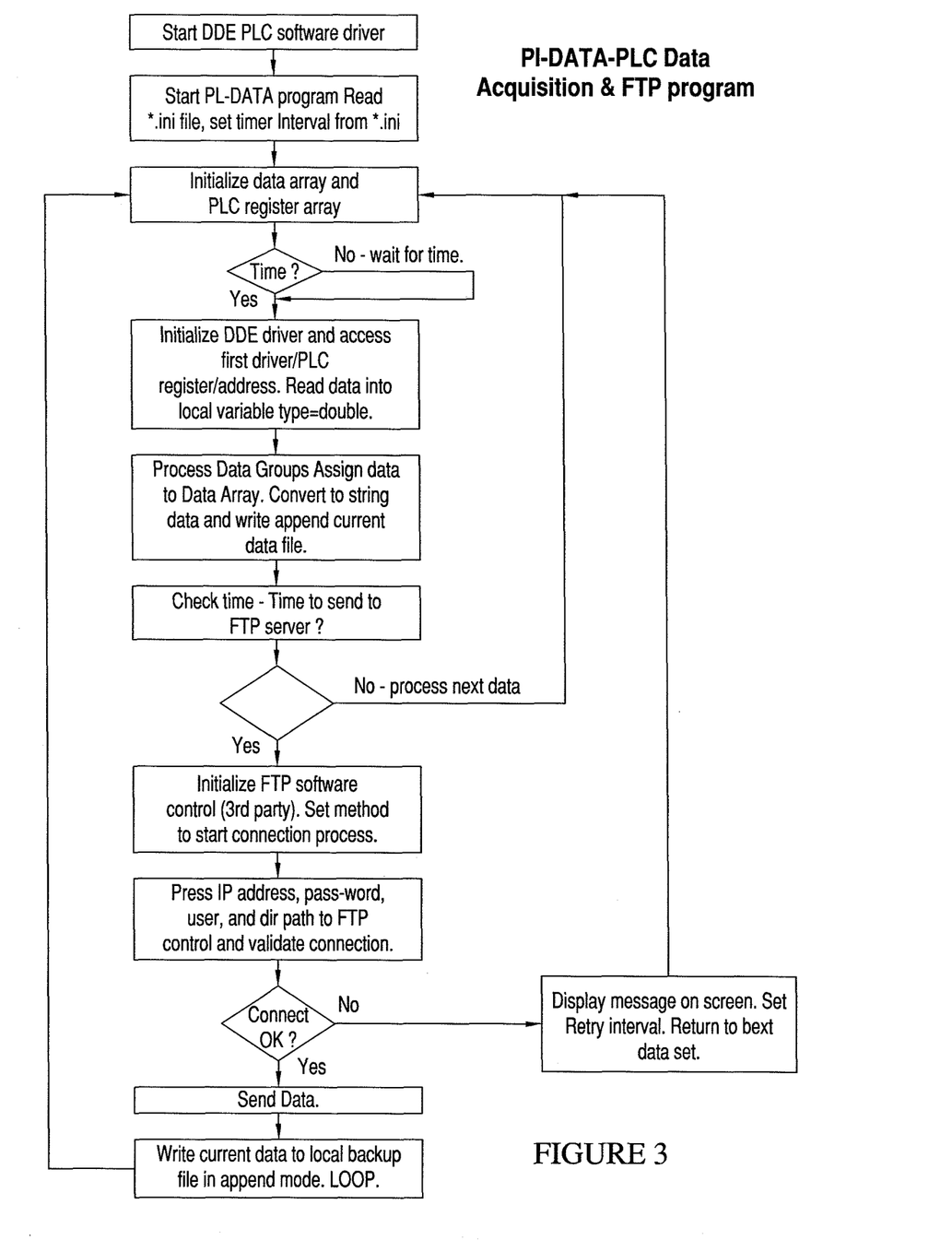
FIG. 3 is a flow diagram of the data acquisition operations of the software.
Figure 4:
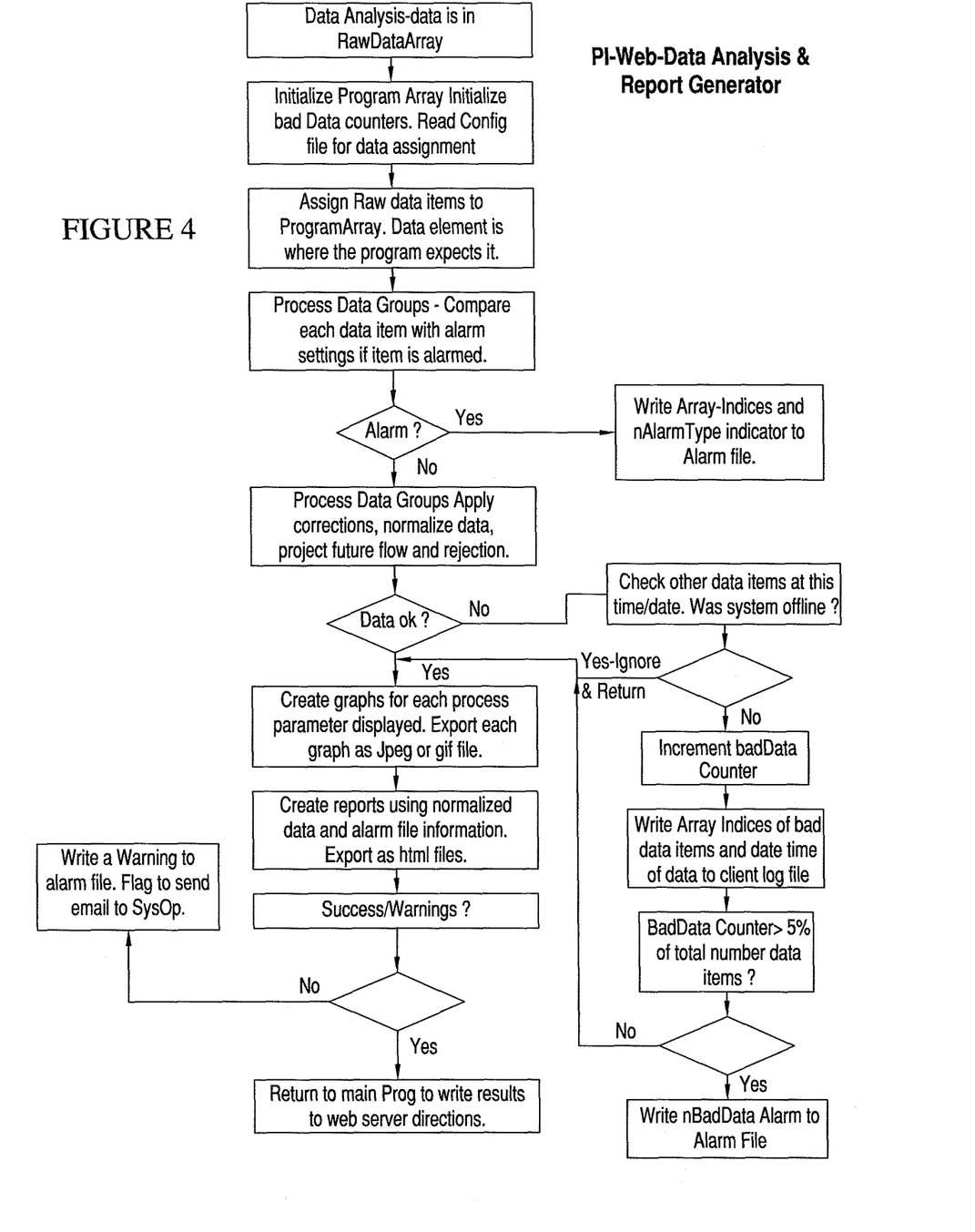
FIG. 4 is a flow diagram of the data analysis and report generator of the software.

Now referring to FIGS. 2-4, set forth is the operation of the program. This program has four essential parts—the local data capture means, the data sending means, the data computation and analysis, and the web server.

At the local site, where the process equipment is located, a serial interface board is used with a local computer to capture data from the process instruments through the serial output of the Programmable Logic Controller (PLC). A software drive specifically designed for the process PLC is utilized for this application. These drivers are available commercially and with the correct driver and some slight modification nearly every commercial PLC can be accessed. This local computer is connected to the Internet either via dial up access or through a dedicated corporate network.

A local configuration file on the local computer tells the program which PLC register addresses to access, any scaling factor which needs to be applied, a physical description of the data being collected for example—temperature or pressure, and how often the access is required. The data set collected is then converted to a comma delimited string value and stored locally on the hard disk in a sequential file. This file may also be encrypted by software if necessary.

At set intervals, usually in the order of 1-30 minutes, the local program calls a third party control software module (the data sending module) which activates the Internet connection software. Either a third party Internet Service Provider is accessed via dial up connection and a modem or a local network is used. The contents of the local data file are then sent via ftp protocol or E-mail (smtp) to either an ftp server which can be accessed by the main data computer or directly to the main data computer. The local computer uses the ftp access path and passwords stored on its hard disk in the configuration file to determine where to send the data. If the configuration file has changed since the last update, this file is also sent.

The local computer program then transfers the contents of the data file to a historical data file on the hard disk providing an on site data backup source. The current data file is then reused for storing new data. Typically the amount of data transferred each cycle to the ftp server is relatively small— several kilobytes—so that the load on the network is minimal. It will also be apparent to anyone skilled in the art of programming that this local computer, if so desired, could also be used to access the Internet and the results of main data computation could be displayed locally.

Main Computer

At the main data computer, the high level program also utilizes a series of configuration of "*.ini" files to establish the path to where the raw data exists. This data is the data which needs to be analyzed, formatted and presented. The configuration file also contains the output path names to the various directories used by each client when they access their data via a web browser.

The main program loops through each data set in turn, restarting as needed. Data is either accessed from the main computer's hard disk or downloaded from the ftp server. The configuration file allows the main program to determine which data point is which part of a typical reverse osmosis or ion exchange system. The configuration file also holds information on which units the local process collects data. For example, the configuration file may indicate that at site B, the third data item in each data set is the applied feed pressure expressed in kilopascals. The program must operate in a consistent set of units and thus translates all pressure values into the common format of pounds per square inch (psi) using a units conversion sub-program. Furthermore, in this example, the feed pressure is critical in determining the future and current performance of the system in reference to its performance when new. Furthermore, for reverse osmosis membranes, changes in pressure are related to age, production rate, and temperature and vice versa. Thus a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. The instant invention does this automatically and reports normalized data to the output.

Of course, many more process parameters are monitored, normalized, and analyzed by the computer software of this invention.

The results of these analyses are then utilized in the following manner:

Raw performance data compared to normalized or corrected data is plotted in simple, easy to understand graphs which are published in the jpeg of gif format readily usable by a web browser.

The performance is compared to predicted normal performance and if the differential exceeds predicted limits (found in the configuration files) selected individuals are automatically sent E-mail or in more extreme cases a pager or fax (paper) alert.

Process and Economic reports are prepared from the data and published as html tables for access by a web browser.

Historical data is regularly updated and new graphs are prepared, in the jpeg or gif format as noted.

Scheduled maintenance requirements are reviewed by the software and if needed within a preset time—usually within one week, or E-mail notification is sent to the designated individual.

In either case, the output is sent to the designated web directories on a web server attached to the Internet. These directories are appropriately protected for access only by authorized individuals. It may be appreciated that the physical location of the Main Data Computer, the ftp server, and the web server may be at the same location or remote from each other. In addition mirror sites can be maintained as necessary to provide reliable service.

The main computer may be either a stand alone unit or can serve as the Internet web server in itself in addition to performing the actual computations. No particular operating system is preferred for the web server and either Windows NT or UNIX may be utilized depending on convenience, reliability, and cost issues.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A system for remotely monitoring the operating performance parameters for a water treatment system, comprising:
    a) at least one sensor assembly effective for monitoring critical water parameters and transmitting operating data via a communications interface;
    b) means for coupling at least one said sensor assembly to an Internet server computer via said communications interface;
    c) means for transmitting said data to a remotely located Internet server computer;
    d) means for storing said transmitted data on said Internet server computer;
    e) means for accessing such data asynchronously from said Internet server computer;
    f) means for manipulating said transmitted and stored data into an analysis result and a report result;
    g) means for uploading said analysis result and said report result to an Internet web server in a format suitable for access and visualization with a web browser computer program;
    h) means for comparing said analysis result with known Federal or State EPA parameters;
    i) means for determining differentials between said known Federal or State EPA parameters and the analysis result; and
    j) means for sending notifications to pre-determined recipients if known limits for differentials are exceeded.

2. The system of claim 1, further including means for filing said report result with an appropriate regulatory agency.

3. The system of claim 1, further including means for transmitting said report result directly to an appropriate regulatory agency using electronic transmission means.

4. The system of claim 3, wherein said electronic transmission means is via e-mail.

5. The system of claim 3, wherein said electronic transmission means is via ftp (file transfer protocol).

6. The system of claim 3, wherein said electronic transmission means is via direct connection over the Internet to a database located on a remote computer.

7. The system of claim 1, wherein said means for manipulating said transmitted and stored data includes routines to notify selected individuals on the basis of the stored parameters relating to the performance of the system being analyzed.

8. The system of claim 1, wherein said means for manipulating said data includes routines to notify selected individuals on the basis of said selected parameters relating to compliance testing dates and performance criteria.

9. The system of claim 1, wherein said means for accessing said operating data from said at least one sensor includes means for reading, querying, and storing data by use of said communications card interface.

10. The system of claim 1, wherein said at least one sensor assembly is operable to transmit operating data in real time.

11. The system of claim 1, further including means for converting said transmitted and stored operating data into visual graphs.

12. The system of claim 1, further including means for converting said transmitted and stored operating data into statistical reports.

13. A non-volatile computer readable medium containing program instructions for remotely monitoring the operating performance parameters for a water treatment system, wherein execution of the program instructions by a computer processing device causes the computer processing device to perform the steps of:
    a) accessing at least one sensor assembly effective for monitoring critical water parameters and transmitting operating data via a communications interface;
    b) coupling at least one said sensor assembly to an Internet server computer via said communications interface;
    c) transmitting said data to a remotely located Internet server computer;
    d) storing said transmitted data on said Internet server computer;

e) accessing such data asynchronously from said Internet server computer;
f) manipulating said transmitted and stored data into an analysis result and a report result;
g) uploading said analysis result and said report result to an Internet web server in a format suitable for access and visualization with a web browser computer program;
h) comparing said analysis result with known Federal or State EPA parameters;
i) determining differentials between said known Federal or State EPA parameters and the analysis result; and
j) sending notifications to pre-determined recipients if known limits for differentials are exceeded.

14. The non-volatile computer readable medium of claim 13, further including a step of filing said report result with an appropriate regulatory agency.

15. The non-volatile computer readable medium of claim 13, further including a step of transmitting said report result directly to an appropriate regulatory agency using electronic transmission means.

16. The non-volatile computer readable medium of claim 13, wherein said step of manipulating said transmitted and stored data includes routines to notify selected individuals on the basis of the stored parameters relating to the performance of the system being analyzed.

17. The non-volatile computer readable medium of claim 13, further including the steps of converting said transmitted and stored operating data into visual graphs.

18. The non-volatile computer readable medium of claim 13, further including the steps of converting said transmitted and stored operating data into statistical reports.

19. A non-volatile computer readable medium containing program instructions for remotely monitoring the operating performance parameters for a water treatment system, wherein execution of the program instructions by a computer processing device causes the computer processing device to perform the steps of:
a) accessing at least one sensor assembly effective for monitoring water parameters and transmitting operating data via a communications interface;
b) coupling at least one said sensor assembly to an Internet server computer via said communications interface;
c) transmitting said data to a remotely located Internet server computer;
d) storing said transmitted data on said Internet server computer;
e) accessing such data from said Internet server computer;
f) manipulating said transmitted and stored data into an analysis result and a report result;
g) uploading said analysis result and said report result to an Internet web server in a format suitable for access and visualization with a web browser computer program;
h) providing a graphical user interface, responsive to said analysis result, configured to display the analyzed data in a color coded graphical display indicating normal system operation, warning status, and alarm conditions, such that an individual having been authorized to access the computer processing device can assess a current state of performance of the water system based on the display;
i) comparing said analysis result with known Federal or State EPA parameters;
j) determining differentials between said known Federal or State EPA parameters and the analysis result; and
k) sending notifications to pre-determined recipients known if limits for differentials are exceeded.

* * * * *